United States Patent
Baker et al.

(10) Patent No.: US 9,579,023 B2
(45) Date of Patent: Feb. 28, 2017

(54) USING NEAR-FIELD COMMUNICATION BOTH FOR OUT-OF-BAND PAIRING AND PHYSIOLOGICAL DATA TRANSFER

(71) Applicant: Welch Allyn, Inc., Skaneateles Falls, NY (US)

(72) Inventors: Steven D. Baker, Beaverton, OR (US); David Harmon Olson, Portland, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 44 days.

(21) Appl. No.: 14/678,127

(22) Filed: Apr. 3, 2015

(65) Prior Publication Data
US 2016/0029889 A1    Feb. 4, 2016

Related U.S. Application Data

(63) Continuation of application No. 13/490,086, filed on Jun. 6, 2012, now Pat. No. 9,008,658.

(51) Int. Cl.
*A61B 5/00* (2006.01)
*G06Q 50/24* (2012.01)
(Continued)

(52) U.S. Cl.
CPC ............ *A61B 5/002* (2013.01); *A61B 5/0024* (2013.01); *A61B 5/411* (2013.01);
(Continued)

(58) Field of Classification Search
CPC ......... A61B 5/002; A61B 5/0024; A61B 5/01; A61B 5/021; A61B 5/0245; A61B 5/411;
(Continued)

(56) References Cited

U.S. PATENT DOCUMENTS 6,868,288 B2    3/2005  Thompson
7,294,105 B1 *  11/2007  Islam ................... A61B 5/0006
                                                    128/903
(Continued)

OTHER PUBLICATIONS

Cooper, Daniel; Motorola intros Elite Sliver and Elite Flip Bluetooth headsets with NFC pairing (video)—IEEE copyright 2011, 5 pages.
(Continued)

*Primary Examiner* — Hai Phan
*Assistant Examiner* — Orlando Bousono
(74) *Attorney, Agent, or Firm* — Merchant & Gould P.C.

(57) ABSTRACT

A method for obtaining physiological data from a medical sensor device includes detecting a proximity of the medical sensor device by an electronic computing device. After the proximity is detected, a message is received from the medical sensor device. A determination is made as to whether the received message includes configuration information for a wireless communication link. When the received message includes the configuration information for the wireless communication link, the wireless communication link is used to receive physiological data from the medical sensor device and the received physiological data is processed at the electronic computing device. When the received message does not include configuration information for the wireless communication link, a determination is made as to whether the received message includes physiological data. When the received message includes the physiological data, the physiological data is processed at the electronic computing device.

15 Claims, 6 Drawing Sheets

(51) Int. Cl.
  *G06Q 10/10* (2012.01)
  *G06F 19/00* (2011.01)
  *H04Q 9/00* (2006.01)
  *A61B 5/01* (2006.01)
  *A61B 5/021* (2006.01)
  *A61B 5/0245* (2006.01)
  *A61B 5/145* (2006.01)

(52) U.S. Cl.
  CPC ......... *G06F 19/3418* (2013.01); *G06Q 10/10* (2013.01); *G06Q 50/24* (2013.01); *H04Q 9/00* (2013.01); *A61B 5/01* (2013.01); *A61B 5/021* (2013.01); *A61B 5/0245* (2013.01); *A61B 5/14542* (2013.01); *H04Q 2209/43* (2013.01)

(58) Field of Classification Search
  CPC A61B 5/14542; G06F 19/3418; G06Q 10/10; G06Q 50/24; H04Q 9/00; H04Q 2209/43
  See application file for complete search history.

(56) References Cited

U.S. PATENT DOCUMENTS

| | | | |
|---|---|---|---|
| 7,958,225 B2 | 6/2011 | Schofield et al. | |
| 8,068,011 B1 | 11/2011 | Sajadi et al. | |
| 8,078,873 B2 | 12/2011 | Shah et al. | |
| 8,210,433 B2 | 7/2012 | Jalkanen et al. | |
| 2004/0102683 A1* | 5/2004 | Khanuja | A61B 5/0002 600/300 |
| 2005/0143671 A1* | 6/2005 | Hastings | A61B 5/411 600/513 |
| 2005/0146431 A1* | 7/2005 | Hastings | A61B 5/002 340/539.12 |
| 2005/0148890 A1* | 7/2005 | Hastings | A61B 5/0006 600/509 |
| 2005/0151640 A1* | 7/2005 | Hastings | A61B 5/411 340/539.11 |
| 2005/0234307 A1* | 10/2005 | Heinonen | A61B 5/0002 600/300 |
| 2006/0094936 A1* | 5/2006 | Russ | A61B 5/0205 600/300 |
| 2006/0183477 A1 | 8/2006 | Bocking et al. | |
| 2006/0293571 A1* | 12/2006 | Bao | G06F 19/322 600/300 |
| 2007/0197878 A1* | 8/2007 | Shklarski | A61B 5/02055 600/300 |
| 2008/0141361 A1 | 6/2008 | Balfanz | |
| 2008/0228045 A1 | 9/2008 | Gao et al. | |
| 2009/0023391 A1 | 1/2009 | Falck | |
| 2009/0231125 A1* | 9/2009 | Baldus | A61B 5/0006 340/539.12 |
| 2010/0070550 A1 | 3/2010 | Hein | |
| 2010/0222648 A1 | 9/2010 | Tan | |
| 2010/0280339 A1* | 11/2010 | Russ | A61B 5/002 600/301 |
| 2010/0315225 A1 | 12/2010 | Teague | |
| 2011/0001605 A1* | 1/2011 | Kiani | G06F 19/327 340/5.6 |
| 2011/0021902 A1 | 1/2011 | Kim et al. | |
| 2011/0105854 A1* | 5/2011 | Kiani | G06F 19/327 600/300 |
| 2011/0221590 A1 | 9/2011 | Baker et al. | |
| 2011/0275907 A1 | 11/2011 | Inciardi et al. | |
| 2011/0288380 A1 | 11/2011 | Inciardi et al. | |
| 2011/0302414 A1 | 12/2011 | Logan et al. | |
| 2012/0001751 A1 | 1/2012 | Baker et al. | |
| 2012/0003933 A1 | 1/2012 | Baker et al. | |
| 2012/0075060 A1* | 3/2012 | Connor | G06F 19/327 340/5.54 |
| 2012/0099566 A1 | 4/2012 | Laine et al. | |

OTHER PUBLICATIONS

Kliem et al.; Towards Self-Organization of Networked Medical Devices, IEEE copyright 2011, 8 pages.
Masihpour et al.; Cooperative Relay in Near Field Magnetic Induction: A New Technology for Embedded Medical Communication Systems, Crown copyright 2010, 6 pages.
Morak et al; Design and Evaluation of a Telemonitoring Concept based on NFC-enabled Mobile Phones and Sensor Devices, IEEE copyright 2011, 7 pages.
Velez et al; Taxonomy of Current Medical Devices for POCT Applications and the Potential Acceptance of Bluetooth Technology for Secure Interoperable Applications, IEEE copyright 2011, 8 pages.
Wang et al.; A Communication Protocol of Wireless Sensor Network for Mobile Healthcare System, IEEE copyright 2010, 6 pages.
International Search Report and Written Opinion issued in PCT/US2013/040482 on Sep. 12, 2013, 9 pages.

* cited by examiner

USING NEAR-FIELD COMMUNICATION BOTH FOR OUT-OF-BAND PAIRING AND PHYSIOLOGICAL DATA TRANSFER

BACKGROUND

In a medical setting, one or more physiological sensor devices may be attached to a patient to obtain physiological data for the patient. One or more of these physiological sensor devices may be wireless devices, permitting a wireless transmission of physiological data from the physiological sensor devices to a patient monitor and to an electronic records system.

A wireless physiological sensor device may include a transceiver, commonly known as a radio, to transmit physiological data using standard wireless communication protocols, such as Bluetooth. However, the cost of a radio is often excessive for a low cost physiological sensor device.

SUMMARY

Embodiments of the disclosure are directed to systems and methods for obtaining physiological data from a medical sensor device. In one aspect, a proximity of the medical sensor device is detected by an electronic computing device. After the proximity is detected, a message is received from the medical sensor device. A determination is made as to whether the received message includes configuration information for a wireless communication link. In response to determining that the received message includes the configuration information for the wireless communication link, the wireless communication link is used to receive physiological data from the medical sensor device and the received physiological data is processed at the electronic computing device. In response to determining that the received message does not include configuration information for the wireless communication link, a determination is made as to whether the received message includes physiological data. In response to determining that the received message includes the physiological data, the physiological data is processed at the electronic computing device.

In another aspect, an electronic computing device comprises a processing unit and system memory. The system memory includes instructions that when executed by the processing unit cause the electronic computing device to detect a proximity of a medical sensor device. When the proximity is detected, a message is received from the medical sensor device. A determination is made as to whether the message includes information to configure a wireless communication link. In response to determining that the received message includes the information to configure the wireless communication link, the wireless communication link is used to receive physiological data from the medical sensor device and the received physiological data is processed. In response to determining that the received message does not include the information to configure the wireless communication link, a determination is made as to whether the received message includes physiological data. In response to determining that the received message includes the physiological data, the received physiological data is processed.

In yet another aspect, a computer-readable data storage medium comprises instructions that, when executed by a processing unit of a patient monitoring device, cause the patient monitoring device to detect a proximity of a medical sensor device. The proximity of the medical sensor device is detected when a determination is made that a distance between the medical sensor device and the patient monitoring device is less than a predetermined threshold. After the proximity of the medical sensor device is detected, a message is received from the medical sensor device. A determination is made as to whether the received message includes configuration information for a wireless communication link. In response to determining that the received message includes the configuration information for the wireless communication link, a Bluetooth connection is established with the medical sensor device, physiological data is received via the Bluetooth connection, the physiological data is sent to the processing unit of the patient monitoring device and the physiological data is displayed on the patient monitoring device. In response to determining that the received message does not include the configuration information for the wireless communication link, a determination is made as to whether the received message includes physiological data. In response to determining that the received message includes the physiological data, the physiological data is extracted from the received message, the physiological data is sent to the processing unit of the patient monitoring device and the physiological data is displayed on the patient monitoring device.

The details of one or more techniques are set forth in the accompanying drawings and the description below. Other features, objects, and advantages of these techniques will be apparent from the description, drawings, and claims.

DETAILED DESCRIPTION

The present disclosure is directed to a system and methods for using near field communication (NFC) for either communicating pairing information for a wireless technology or for transmitting physiological data from a wireless physiological sensor device. NFC is a set of standards for establishing communication between wireless devices by touching the wireless devices together or bringing the wireless devices into close proximity with each other. Non-standards-based NFC solutions may also be used.

Using the systems and methods, when physiological sensor devices that are attached to a patient include a transceiver, such as a radio, NFC may communicate pairing information between a patient monitor device and a physiological sensor device establish a wireless connection between a physiological sensor device and the patient monitor device. When the wireless connection is established, physiological data and patient identification information may be transmitted via the wireless connection from the physiological sensor device to the patient monitor device.

When a physiological sensor device does not include a radio, physiological data from the physiological sensor device may be transmitted directly via NFC to the patient monitor device. Using the systems and methods, a determination is automatically made as to whether NFC received data is physiological data or pairing data.

In addition, patient identification may be transmitted from the patient monitor device to the physiological sensor device. Subsequently, the patient identification may be transmitted to a different patient monitor device or mobile electronic device such as a personal data assistance (PDA), cellular phone, laptop, tablet, or similar devices.

Various methods of proximity detection may be used to determine whether the wireless devices are within close proximity of each other. Some example methods of proximity detection include received signal strength indication (RSSI) methods such as standard Bluetooth, Bluetooth Low Energy (BTLE) and WiFi. Other example methods of proximity detection include differential methods such as differential global positioning (GPS), ultra-wideband (UWB), infrared (IR), infrared data association (IRDA) and NFC. Proximity detection methods such as IRDA, UWB and NFC typically use both standard and proprietary data transport mechanisms. Proximity detection may be wireless or proximity detection may use a physical connection. In examples, proximity detection may occur when two devices are within two inches of each other, although other distances may be used.

Figure 1:
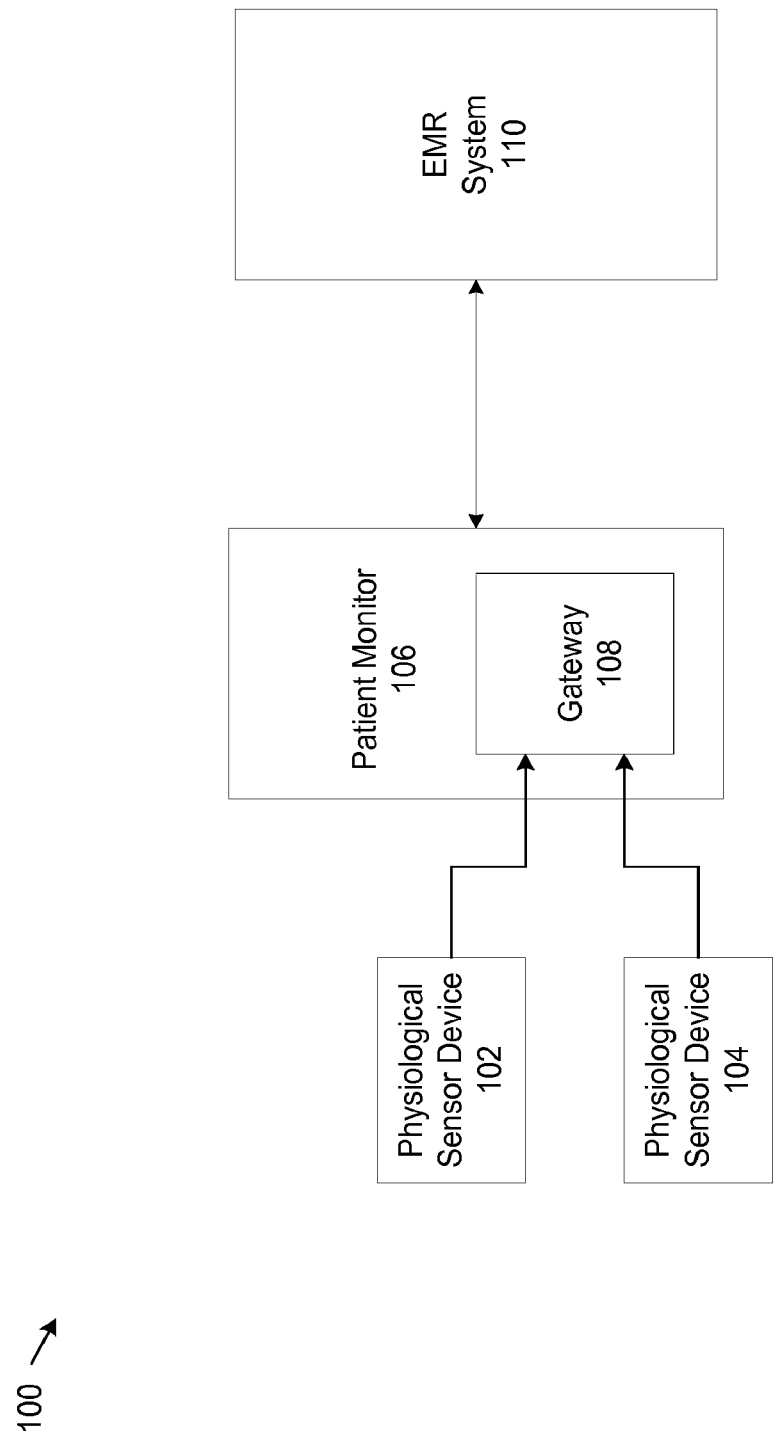
FIG. 1 shows an example system that supports the use of near-field communication for both out-of-band pairing and physiological data transfer.

FIG. 1 shows an example system 100 in which NFC may be used. The example system 100 includes physiological sensor devices 102, 104, a patient monitor device 106, a gateway device 108 and an electronic medical records (EMR) system 110. In this disclosure, the EMR system 100 may be an electronic health record (EHR) system. The physiological sensor devices 102, 104 monitor physiological data from a patient (not shown). An example of physiological sensor devices 102, 104 is a thermometer. Other examples may include an oxygen saturation (SPO2) sensor, an ECG sensor, a blood pressure sensor, an ophthalmoscope, etc. In system 100, physiological sensor device 102 is a wireless thermometer and does not include a radio device. Physiological sensor device 104 is an ECG sensor and does include a radio device. More than two physiological sensor devices may be used. In this disclosure, an NFC subsystem is not considered to be a radio device.

The patient monitor device 106 receives physiological data from physiological sensor devices 102, 104 and displays the received physiological data on a display screen on the patient monitor device 106. The patient monitor device 106 may also send the received physiological data to the EMR system 110. An example of the patient monitor device 106 is the Welch Allyn 1500 Patient Monitor from Welch Allyn, Inc. of Skaneateles Falls, N.Y. Other examples are possible.

In the example system 100, the patient monitor device 106 includes the gateway device 108. The gateway device 108 is a component of the patient monitor device 106 that receives data from physiological sensor devices 102, 104, parses the data and determines whether the data represents pairing information or physiological data. When the data represents physiological data, the physiological data is typically displayed on the patient monitor device 106 and also sent to the EMR system 110. When the data represents pairing information (wireless configuration data), the gateway typically extracts configuration data from the pairing data. Using a wireless communication protocol, a wireless connection is established between physiological sensor device 104 and patient monitor device 106. After the wireless connection is established, physiological data (for example ECG data) is transmitted from physiological sensor device 104 to patient monitor device 106.

In operation, the gateway device 108 periodically transmits a signal that can be detected by a sensor device, for example by physiological sensor device 102, using NFC. When physiological sensor device 102 comes within range of patient monitor device 106, patient monitor device 106 detects the presence of physiological sensor device 102. In examples, patient monitor device 106 detects the presence of physiological sensor device 102 when NFC circuits in physiological sensor device 106 load-modulate the signal transmitted from gateway device 108. The gateway device 108 then transmits a continuous-wave signal to physiological sensor device 102. In examples, the continuous-wave signal is inductively coupled to the physiological sensor device 102. In other examples, a range between physiological sensor device 102 and patient monitor device 106 may be detected via signal strength or via time delay of arrival.

In examples, the wireless connection is established using the Bluetooth communication standard. When Bluetooth is used, pairing information is transmitted via NFC using an out-of-band Bluetooth communication channel. When the wireless connection is established, physiological data is transmitted over the wireless connection using an in-band Bluetooth communication channel. In other examples, the wireless connection may be established using a personal area network (PAN) or a body area network (BAN). When the PAN or BAN is used, the physiological data is transmitted over a PAN or BAN wireless connection. Pairing information may also be transmitted using other methods, as identified in the Bluetooth 2.1+EDR standard.

The EMR system 110 is an electronic medical records system. The EMR system 110 typically receives and stores data from patient monitor device 106 and from other patient monitor devices in the example system 100. The EMR system 110 also stores patient identification and other medical record information.

Figure 2:
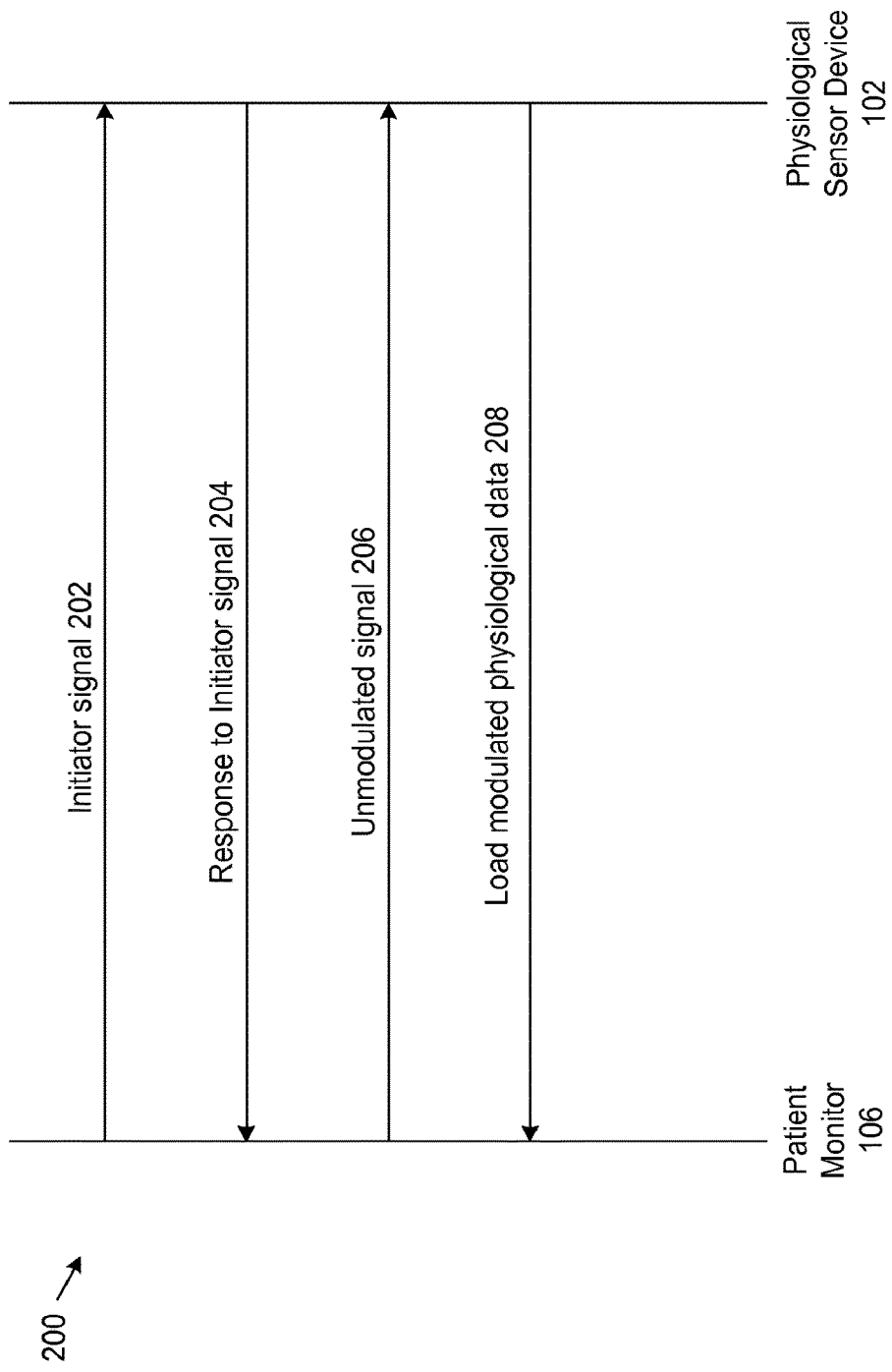
FIG. 2 shows an example communication scheme between a physiological sensor device and the patient monitor device of FIG. 1.

FIG. 2 shows an example communication scheme 200 between patient monitor device 106 and physiological sensor device 102. As discussed, physiological sensor device 102 is a wireless thermometer and does not include a radio device. Therefore, for the example communication scheme 200, the physiological sensor device uses NFC to send physiological data to the patient monitor device 106.

The patient monitor device 106 transmits an initiator signal 202. The initiator signal can be detected by the physiological sensor device 102 when the physiological sensor device 102 is within range of the patient monitor device. In examples, the range may be from 0.5 inches to 3 inches. Other ranges are possible. The initiator signal may be transmitted periodically to save power or the initiator signal may be a continuous-wave signal. When the initiator signal is transmitted periodically, the initiator signal is typically a small pulse.

When the physiological sensor device 102 comes within range of the patient monitor device 106, the physiological sensor device 102 sends response to initiator signal 204 to the patient monitor device 106. When the physiological sensor device 102 is configured for NFC using card-emulation mode, the response to initiator signal 204 is typically a load-modulated signal. Because wireless sensor devices are typically power limited, examples in this disclosure are oriented towards NFC using card-emulation mode. However, this disclosure is not limited to card-emulation mode, and other NFC modes, for example peer-to-peer mode, may be used.

When the patient monitor device 106 receives the response to initiator signal 204, the patient monitor device 106, having determined a card-emulation protocol, sends an un-modulated signal 206 to physiological sensor device 102. The un-modulated signal 206 is typically a continuous wave signal. In examples, the un-modulated signal 206 is inductively coupled to circuitry in the physiological sensor device 102.

As a result of receiving the inductively coupled un-modulated signal 206, the physiological sensor device 102 load modulates the un-modulated signal 206 with physiological data from the physiological sensor device 102. The physiological sensor device 102 then sends the physiological data via load modulated physiological data signal 208 to the patient monitor device 106. An NFC receiver in the patient monitor device 106 converts the load modulated physiological data signal 208 into a digital signal for processing at the patient monitor device 106, as explained later herein.

In examples, physiological sensor device 102 may also include patient identification information in the load modulated physiological data signal 208. The patient identification permits physiological sensor device 102 to transmit patient context information to any patient monitor device or mobile electronic device to which the physiological sensor device 102 is proximal. In examples, physiological sensor device 102 may have received the patient identification information from patient monitor device 106, for example during an earlier connection when physiological sensor device 102 was proximal to patient monitor device 106.

Figure 3:
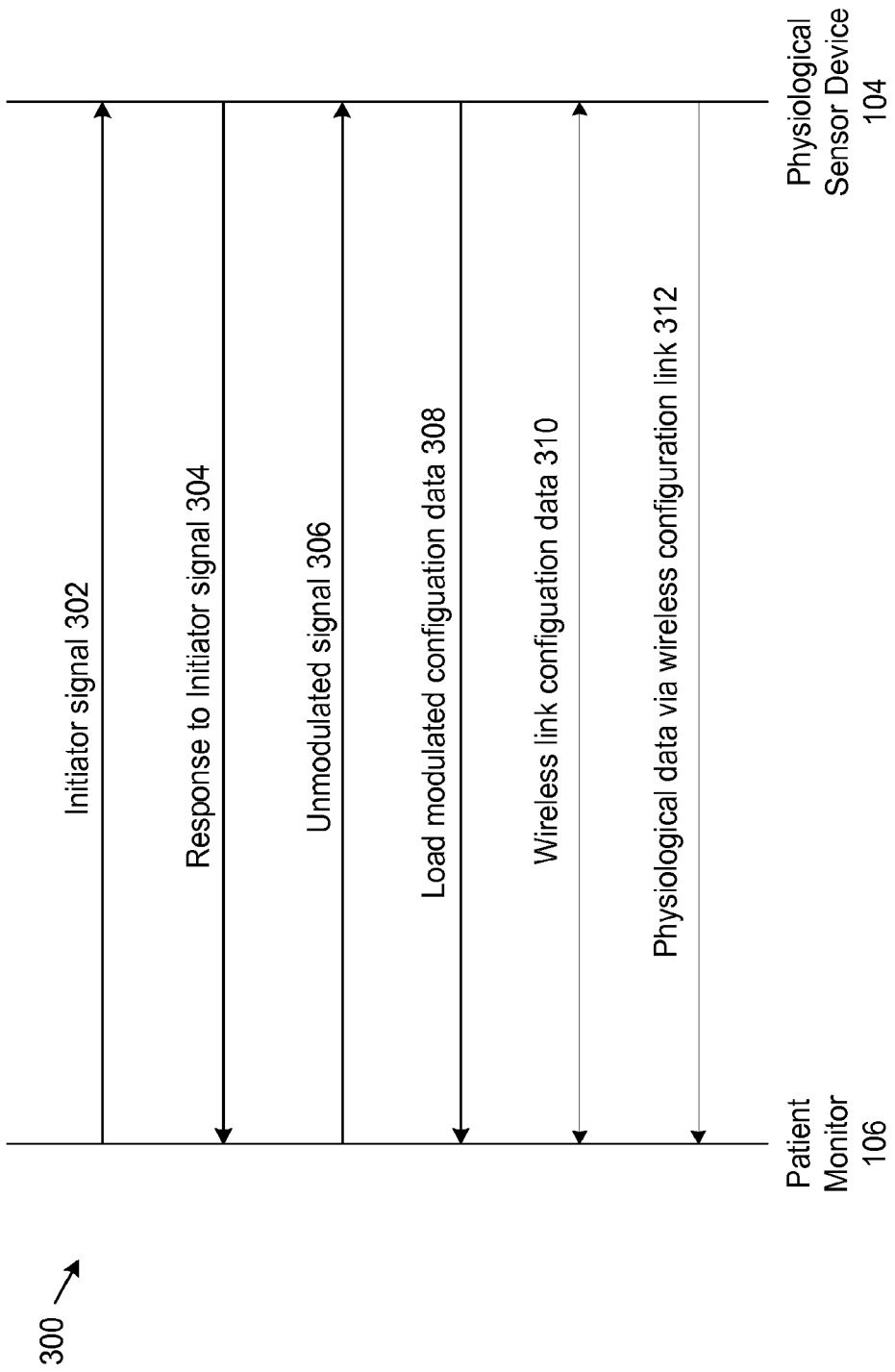
FIG. 3 shows an alternate communication scheme between a physiological sensor device and the patient monitor device of FIG. 1.

FIG. 3 shows an example communication scheme 300 between patient monitor device 106 and physiological sensor device 104. As discussed, physiological sensor device 104 is a wireless ECG device and includes a radio device. Therefore, for example communication scheme 300, the physiological sensor device 104 uses NFC to establish a wireless connection, typically a Bluetooth connection, between the physiological sensor device 104 and patient monitor device 106. Physiological data is sent from physiological sensor device 104 to patient monitor device 106 over the wireless connection. In examples, as discussed, patient identification information from physiological sensor device 104 may be included with the physiological data.

As discussed, the patient monitor device 106 transmits an initiator signal, in this example initiator signal 302. Initiator signal 302 may include capability information for the patient monitor device 106, such as supported protocols. When the physiological sensor device 104 comes within range of the patient monitor device 106, the physiological sensor device 104 sends response to initiator signal 304 to the patient monitor device 106. The response to initiator signal 304 confirms to the patient monitor device 106 that there is a proximal device with which to connect and includes any handshakes to negotiate the NFC protocol. The response to the initiator signal may be load modulated. A protocol for establishing the NFC connection is defined in ISO standards for NFC, for example ISO 14443 A-1, A-2, A-3, B-1, B-2, B-3, ISO 15693-3, -2, -1, and ISO 18092.

When the patient monitor device 106 receives the response to initiator signal 304, the patient monitor device 106, sends an un-modulated signal 306 to physiological sensor device 104. The un-modulated signal is typically a continuous-wave signal. In examples, the un-modulated signal 306 is inductively coupled to circuitry in the physiological sensor device 104.

As a result of receiving the inductively coupled un-modulated signal 306, the physiological sensor device 104 load modulates the un-modulated signal 306 with radio configuration data from the physiological sensor device 104 and sends the load-modulated configuration data signal 308 to patient monitor 106. The load-modulated configuration data is used to initiate a wireless connection, typically a Bluetooth connection, between the physiological sensor device 104 and the patient monitor device 106. Other wireless connections may be used. Wireless link configuration data 310 is sent between patient monitor device 106 and physiological sensor device 104.

The physiological sensor device 104 then sends physiological data 312 to the patient monitor device 106 using the wireless connection. As explained later herein, when the patient monitor device 106 receives the physiological data 312 from the physiological sensor device 104, the gateway 108 parses the physiological data 312. The gateway 108 parses data received from physiological sensor devices 102, 104 to determine whether the data is physiological data, out-of-band pairing data or some other information, such as a link to the patient's EMR, a link to download new software.

Figure 4:
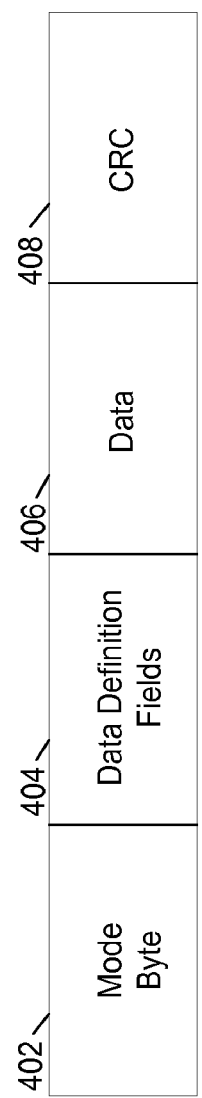
FIG. 4 shows an example format of data received at the patient monitor device of FIG. 1.

FIG. 4 shows an example format of data 400 received at patient monitor device 106 from physiological sensor devices 102, 104. The example data 400 includes a mode byte 402, a data definition field 404, a data field 406 and a CRC 408.

The example mode byte 402 defines whether the data 400 comprises a direct transmission of the physiological data 312, whether the data 400 includes out-of-band pairing information, or other information. When the data 400 comprises the direct transmission of the physiological data, the mode byte 402 is set to a constant numerical value that represents direct transmission of physiological data. When the data 400 includes out-of-band pairing information, the mode byte 402 is set to a constant numerical value that indicates that the data 400 includes the out-of-band pairing information.

When the mode byte 402 is set to the value that represents the direct transmission of physiological data, the example data definition fields 404 defines a type of data that is being transmitted. For example, if temperature is being transmitted, the data definition fields 404 may include one field that represents temperature and another field that represents units of temperature. As another example, if SPO2 is being transmitted, the data definition fields 404 may include one field that represents SPO2 and another field that represents units of SPO2. The data definition fields may also describe the length of the data field.

The data field 406 includes the actual physiological data being transmitted. For example, if temperature is being transmitted, the data field 406 may include a byte having a numerical value of 98.6.

The CRC byte 408 includes a cyclic redundancy code value for bytes 402 through 406. When the data 400 is received at the patient monitor device 106, the patient monitor device 106 performs a CRC check on bytes 402 through 406. The patient monitor device 106 then compares the result of the CRC check with the CRC byte 408 to validate the integrity of the data in bytes 402 through 406.

In addition to using NFC with medical sensor devices and patient monitor devices, mobile devices, for example smart telephones including the HTC One X, may include an NFC transceiver. A clinician, for example a nurse, may use NFC in conjunction with a smart telephone to obtain physiological data from a medical sensor device and from a patient monitor device. In an example workflow, a clinician, for example a nurse, may touch the smart telephone to an ID bracelet on a patient. Touching the smart telephone to the ID bracelet may start a software application on the smart telephone that displays an EMR record for the patient. Using a wireless thermometer with NFC, the nurse may take the patient's temperature. When the nurse touches the thermometer with the smart telephone, temperature data for the patient is transmitted via NFC from the thermometer to the smart telephone. In examples, other medical sensor devices may transmit physiological data via NFC to a smart telephone.

In other example workflows, the patient monitor device 106 may include one or more medical sensor devices. The medical sensor devices may be hard-wired to the patient monitor device 106. For example, the patient monitor device 106 may include a medical sensor device for obtaining non-invasive blood pressure (NIBP) for a patient. A blood pressure cuff may be physically connected to the patient monitor device 106 via tube. Other medical sensor devices that may be physically connected to the patient monitor device 106 include a thermometer, glucometer, ECG, ETCO2, and a SPO2 sensor device. In one example workflow, a nurse or other clinician may use NFC in conjunction with a mobile electronic device, such as a smart telephone, to obtain physiological data for a patient directly from the patient monitor device 106. In this example workflow, when the smart telephone comes within a proximity of the patient monitor device 106 or physically touches the patient monitor device 106, physiological data stored at the patient monitor device 106 may be transmitted via NFC to the smart telephone. The transmission of the physiological data may include patient identification information and connection information for an EMR for the patient. Including the connection information may result in the EMR being automatically loaded on the smart telephone. A clinician identifier stored in the smart telephone may be appended to the EMR to provide accounting information of the clinician interaction with the patient.

Figure 5:
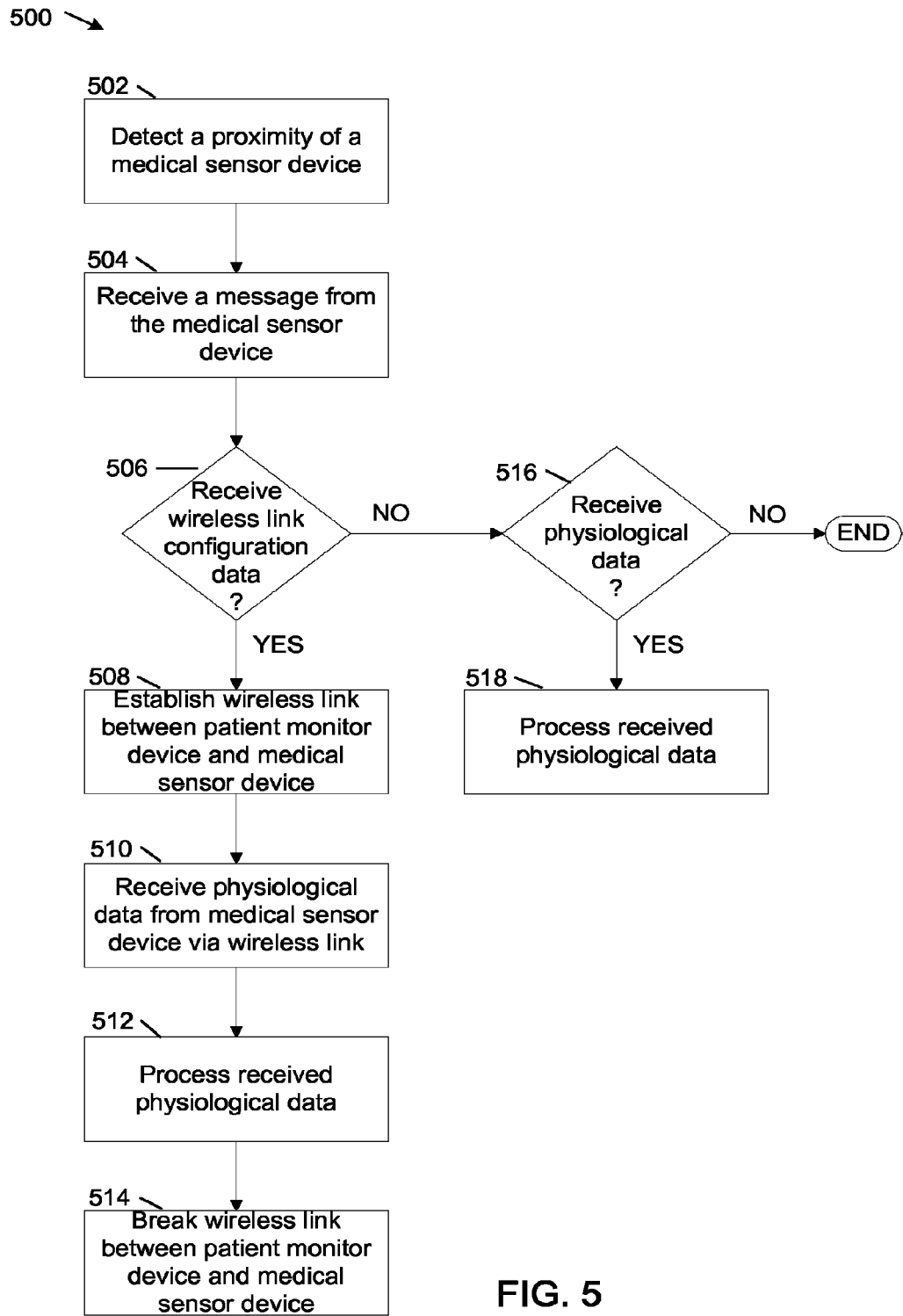
FIG. 5 shows an example method for using near-field communications for pairing and physiological data transfer.

FIG. 5 shows an example flowchart for a method 500 for using NFC for both out-of-band pairing and physiological data transfer. The physiological data is obtained from a wireless medical sensor device, for example from physiological sensor device 102.

At operation 502, at a patient monitor device, for example patient monitor device 106, a proximity of the medical sensor device is detected via NFC. In examples, the proximity may be detected by moving the medical sensor device within a predetermined range, for example two inches, of the patient monitor device 106 or by having the medical sensor device make contact with the patient monitor device 106. In examples, the patient monitor device 106 may be a handheld device and the patient monitor device 106 may be moved to a proximity of the medical sensor device. The medical sensor device is a sensor device that obtains physiological data from a patient. Examples of the medical sensor device include a wireless thermometer, a wireless SPO2 sensor, a wireless ECG device, etc.

The patient monitor device 106 transmits initiation signals to the surrounding area. When the medical sensor device comes into the proximity of the patient monitor device 106, the medical sensor device receives an initiation signal. At operation 504, after the proximity of the medical sensor device is detected, the patient monitor device 106 receives a message, via NFC, from the medical sensor device. The message comprises a response to the initiation signal. In examples, the message may include physiological data from the medical sensor device or the message may include configuration data used to set-up a wireless communication link between the patient monitor device 106 and the medical sensor device.

At operation 506, a determination is made as to whether the message includes the wireless communication link configuration data. The determination is made by evaluating mode byte 402 in the received data. The mode byte indicates with the received message includes physiological data or configuration data. The configuration data constitutes pairing information for the wireless communication link.

When a determination is made that the message includes the wireless communication link configuration data, at operation 508, a wireless communication link is established between the patient monitor device 106 and the medical sensor device. The wireless communication link is set-up via a protocol associated with the wireless communication link. For example, if the wireless communication link is set up using the Bluetooth communication standard, a Bluetooth address of a radio on the patient monitor device 106 is sent to the medical sensor device and a Bluetooth address of a radio on the medical sensor device is sent to patient monitor device 106. Using NFC, a wireless connection is established between the patient monitor device 106 and the medical sensor device using the Bluetooth addresses. A link key is randomly generated and communicated between the patient monitor device 106 and the medical sensor device and a secure connection is established.

At operation 510, physiological data from the medical sensor device is received at the patient monitor device 106 via the established wireless communication link. Examples of physiological data include a temperature of a patient, an SPO2 reading for the patient and ECG data for the patient.

At operation 512, the received physiological data is processed at the patient monitor device. Processing the physiological data includes parsing, storing and displaying the received physiological data at the patient monitor device 106. In examples, the received physiological data may also be transmitted to an EMR system, for example EMR system 110, for further processing and storage.

At operation 514, the wireless connection between the medical sensor device and the patient monitor device 106 is broken. Breaking the wireless connection also breaks a pairing between the medical sensor device and the patient monitor device 106. Breaking the pairing prevents the medical sensor device from transmitting data to a wrong patient monitoring device, if, for example, the medical sensor device is moved to a new location. For continuous monitoring, as long as a continuous physiological signal is detected, operation 514 may not be executed.

At operation 506, when a determination is made that the received message does not include the wireless communications link configuration data, at operation 516, a determination is made as to whether the received message includes physiological data from the medical sensor device.

When it is determined at operation 516 that the received message includes the physiological data from the medical sensor device, at operation 518 the physiological data is processed at the patient monitor device 106. The processing of the physiological data includes parsing the data definition field 404 of the received message to determine the type of physiological data received. The processing of the physiological data also includes storing and displaying the physiological data at the patient monitor device 106 and transmitting the physiological data to the EMR system 110. Breaking the connection between the medical sensor device and the patient monitor device 106 is typically not required because an NFC link between the medical sensor device and the patient monitor device 106 can only exist when the medical sensor device and the patient monitor device 106 are proximal. NFC does not support a concept of a communication session as, for example, with a Bluetooth radio.

Figure 6:
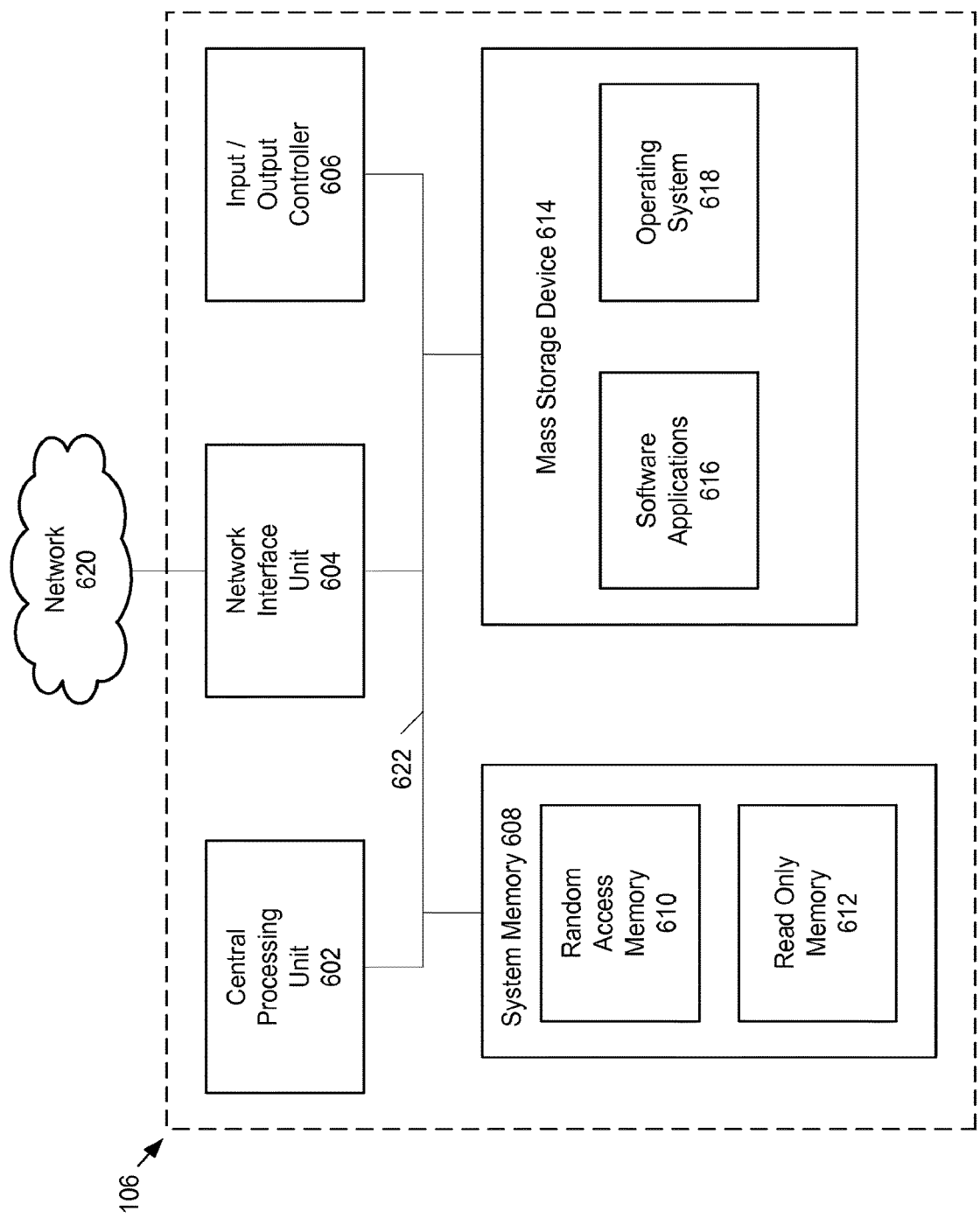
FIG. 6 shows example physical components of the patient monitor device of FIG. 1.

FIG. 6 illustrates example physical components of the patient monitor device 106. As illustrated in the example of FIG. 6, the patient monitor device 106 includes at least one central processing unit ("CPU") 602, a system memory 608, and a system bus 622 that couples the system memory 608 to the CPU 602. The system memory 608 includes a random access memory ("RAM") 610 and a read-only memory ("ROM") 612. A basic input/output system contains the basic routines that help to transfer information between elements within the patient monitor device 106, such as during startup, is stored in the ROM 612. The patient monitor device 106 further includes a mass storage device 614. The mass storage device 614 is able to store software instructions and data.

The mass storage device 614 is connected to the CPU 602 through a mass storage controller (not shown) connected to the bus 622. The mass storage device 614 and its associated computer-readable data storage media provide non-volatile, non-transitory storage for the patient monitor device 106. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the patient monitor device 106.

According to various embodiments of the invention, the patient monitor device 106 may operate in a networked environment using logical connections to remote network devices through the network 620, such as a local network, the Internet, or another type of network. The patient monitor device 106 may connect to the network 620 through a network interface unit 604 connected to the bus 622. It should be appreciated that the network interface unit 604 may also be utilized to connect to other types of networks and remote computing systems. The patient monitor device 106 also includes an input/output controller 606 for receiving and processing input from a number of other devices, including a keyboard, a mouse, a touch user interface display screen, or another type of input device. Similarly, the input/output controller 606 may provide output to a touch user interface display screen, a printer, or other type of output device.

As mentioned briefly above, the mass storage device 614 and the RAM 610 of the patient monitor device 106 can store software instructions and data. The software instructions include an operating system 618 suitable for controlling the operation of the patient monitor device 106. The mass storage device 614 and/or the RAM 610 also store software instructions, that when executed by the CPU 602, cause the patient monitor device 106 to provide the functionality of the patient monitor device 106 discussed in this document. For example, the mass storage device 614 and/or the RAM 610 can store software instructions that, when executed by the CPU 602, cause the patient monitor device 106 to display received physiological data on the display screen of the patient monitor device 106.

The various embodiments described above are provided by way of illustration only and should not be construed to be limiting. Various modifications and changes may be made to the embodiments described above without departing from the true spirit and scope of the disclosure.

What is claimed is:

1. A method for obtaining physiological data from a medical sensor device, the method comprising:

detecting a proximity of the medical sensor device by an electronic computing device, wherein the electronic computing device is a mobile computing patient monitoring device, the proximity of the medical sensor device being detected when a determination is made that a distance between the medical sensor device and the electronic computing device is less than a predetermined threshold;

after the proximity is detected, receiving a message from the medical sensor device, wherein the message includes at least one of configuration information for establishing a wireless communication link and physiological data;

after the message is received, determining whether the received message includes the configuration information for establishing the wireless communication link, wherein the configuration information includes data used to initiate a wireless connection between the electronic computing device and the medical sensor device;

in response to determining that the received message includes the configuration information for establishing the wireless communication link:
      establishing the wireless communication link between the electronic computing device and the medical sensor device;
      using the wireless communication link to receive physiological data from the medical sensor device;
      sending the physiological data received from the medical sensor device to a processing unit of the electronic computing device; and
      processing the physiological data received from the medical sensor device by the electronic computing device; and when the received message does not include the configuration information for establishing the wireless communication link:
      determining whether the received message includes the physiological data; and
      in response to determining that the received message includes the physiological data;
      extracting the physiological data from the received message;
      sending the extracted physiological data to the processing unit of the electronic computing device;
      processing the extracted physiological data at the electronic computing device; and
      displaying the extracted and processed physiological data on the electronic computing device.

2. The method of claim 1, wherein detecting the proximity of the medical sensor device comprises sending a first signal from the electronic computing device.

3. The method of claim 2, wherein detecting the proximity of the medical sensor device further comprises receiving a second signal from the medical sensor device.

4. The method of claim 1, wherein using the wireless communication link to receive physiological data from the medical sensor device comprises:
establishing a Bluetooth connection with the medical sensor device; and
receiving the physiological data via the Bluetooth connection.

5. The method of claim 4, wherein the Bluetooth connection is a secure connection.

6. The method of claim 1, wherein a near-field communication connection is established between the mobile computing patient monitoring device and the medical sensor device and, after the near-field communication connection is established, patient identification information from the medical sensor device is received at the mobile computing patient monitoring device.

7. The method of claim 1, wherein a near-field communication connection is established between the mobile computing patient monitoring device and a different patient monitoring device and, after the near-field communication connection is established, patient identification information from the mobile computing patient monitoring device is received at the different patient monitoring device.

8. The method of claim 1, wherein the received message includes one or more data definitions corresponding to the physiological data received from the medical sensor device.

9. The method of claim 1, further comprising, after the physiological data is received from the medical sensor device, breaking the wireless communication link between the medical sensor device and the electronic computing device.

10. An electronic computing device, wherein the electronic computing device is a mobile computing patient monitoring device, the electronic computing device comprising:
a processing unit; and
system memory, the system memory including instructions that when executed by the processing unit cause the electronic computing device to:
detect a proximity of a medical sensor device, the proximity of the medical sensor device being detected when a determination is made that a distance between the medical sensor device and the electronic computing device is less than a predetermined threshold;
after the proximity is detected, receive a message from the medical sensor device, wherein the message includes at least one of configuration information for establishing a wireless communication link and physiological data;
after the message is received, determine whether the received message includes the configuration information for establishing the wireless communication link, wherein the configuration information includes data used to initiate a wireless connection between the electronic computing device and the medical sensor device;
in response to determining that the received message includes the configuration information to configure for establishing the wireless communication link:
establish the wireless communication link between the electronic computing device and the medical sensor device;
use the wireless communication link to receive physiological data from the medical sensor device;
send the physiological data received from the medical sensor device to the processing unit of the electronic computing device; and
process the physiological data received from the medical sensor device; and
when the received message does not include the configuration information for establishing the wireless communication link:
determine whether the received message includes the physiological data; and
in response to determining that the received message includes the physiological data;
extract the physiological data from the received message;
send the extracted physiological data to the processing unit of the electronic computing device;
process the extracted physiological data at the electronic computing device; and
display the extracted and processed physiological data on the electronic computing device.

11. The electronic computing device of claim 10, wherein use of the wireless communication link to receive the physiological data from the medical sensor device comprises:
establish a personal area network (PAN) connection or a body area network (BAN) connection with the medical sensor device; and
obtain the physiological data via the PAN or BAN connection.

12. The electronic computing device of claim 10, further comprising:
after the proximity is detected but before the message is received from the medical sensor device, transmit a continuous-wave radio-frequency signal from the electronic computing device;
after the message is received, determine that the received message is a load-modulated signal; and
convert the load-modulated signal into a digital data signal.

13. The electronic computing device of claim 10, wherein a near-field communication connection is established between the mobile computing patient monitoring device and a different patient monitoring device and, after the near-field communication connection is established, patient identification information from the mobile computing patient monitoring device is received at the different patient monitoring device.

14. The electronic computing device of claim 10, further comprising after the physiological data is received from the medical sensor device, break the wireless communication link between the medical sensor device and the electronic computing device.

15. A non-transitory, computer-readable data storage medium comprising instructions that, when executed by a processing unit of a mobile computing patient monitoring device, cause the mobile computing patient monitoring device to:
detect a proximity of a medical sensor device, the proximity of the medical sensor device being detected when a determination is made that a distance between the medical sensor device and the mobile computing patient monitoring device is less than a predetermined threshold;
after the proximity of the medical sensor device is detected, receive a message from the medical sensor device, wherein the message includes at least one of configuration information for establishing a wireless communication link and physiological data;

after the message is received, determine whether the received message includes the configuration information for establishing the wireless communication link, wherein the configuration information includes data used to initiate a wireless connection between the mobile computing patient monitoring device and the medical sensor device;

in response to determining that the received message includes the configuration information for establishing the wireless communication link:
  establish the wireless communication link between the mobile computing patient monitoring device and the medical sensor device;
  use the wireless communication link to receive physiological data from the medical sensor device;
  send the physiological data received from the medical sensor device to the processing unit of the mobile computing patient monitoring device; and
  process the physiological data received from the medical sensor device by the mobile computing patient monitoring device; and when the received message does not include the configuration information for establishing the wireless communication link;
  determine whether the received message includes the physiological data; and
  in response to determining that the received message includes the physiological data:
    extract the physiological data from the received message;
    send the extracted physiological data to the processing unit of the mobile computing patient monitoring device;
    process the extracted physiological data at the mobile computing patient monitoring device; and
    display the extracted and processed physiological data on the mobile computing patient monitoring device.

* * * * *